(12) United States Patent
Kim et al.

(10) Patent No.: US 11,904,227 B2
(45) Date of Patent: Feb. 20, 2024

(54) EXERCISE INFORMATION MANAGEMENT SYSTEM AND METHOD OF CONTROLLING THE SAME

(71) Applicants: Hyundai Motor Company, Seoul (KR); Kia Motors Corporation, Seoul (KR)

(72) Inventors: Sung Un Kim, Gyeonggi-do (KR); Jeongwoo Nahm, Gyeonggi-do (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 61 days.

(21) Appl. No.: 17/108,177

(22) Filed: Dec. 1, 2020

(65) Prior Publication Data

US 2021/0322851 A1    Oct. 21, 2021

(30) Foreign Application Priority Data

Apr. 16, 2020   (KR) ........................ 10-2020-0045980

(51) Int. Cl.
| | |
|---|---|
| G09B 21/00 | (2006.01) |
| A63B 71/06 | (2006.01) |
| G16H 20/30 | (2018.01) |
| G16H 40/67 | (2018.01) |
| H04L 9/40 | (2022.01) |
| A63B 24/00 | (2006.01) |
| G06F 3/0481 | (2022.01) |

(Continued)

(52) U.S. Cl.
CPC ...... *A63B 71/0622* (2013.01); *A63B 24/0062* (2013.01); *G16H 20/30* (2018.01); *G16H 40/67* (2018.01); *H04L 63/08* (2013.01); *A63B 2071/065* (2013.01); *A63B 2071/0675* (2013.01); *A63B 2071/0694* (2013.01); *A63B 2220/807* (2013.01); *A63B 2220/833* (2013.01); *A63B 2225/12* (2013.01); *A63B 2230/60* (2013.01); *G06F 3/0481* (2013.01); *G06V 40/10* (2022.01); *G09B 19/003* (2013.01)

(58) Field of Classification Search
CPC ............ G06F 3/013; G09B 21/00; A61F 4/00
See application file for complete search history.

(56) References Cited

U.S. PATENT DOCUMENTS

| | | | |
|---|---|---|---|
| 2011/0056102 A1* | 3/2011 | Reid .................. | A47G 1/02 40/219 |
| 2013/0171601 A1* | 7/2013 | Yuasa ................ | G06V 40/23 434/258 |

(Continued)

FOREIGN PATENT DOCUMENTS

WO    WO-2019231982 A1 *  12/2019  ............. A45D 42/00

*Primary Examiner* — Kesha Frisby
(74) *Attorney, Agent, or Firm* — Fox Rothschild LLP (57) ABSTRACT

An exercise information management system and a method of controlling the exercise information management system are provided. The exercise information management system includes a plurality of smart mirrors and a server that communicates with at least one smart mirror. Exercise-related information of an exercise performed by a user in the at least one smart mirror among the plurality of smart mirrors is stored in the server and remaining smart mirrors among the plurality of smart mirrors is configured to share the exercise-related information stored in the server.

20 Claims, 7 Drawing Sheets

(51) Int. Cl.
  *G09B 19/00* (2006.01)
  *G06V 40/10* (2022.01)

(56) References Cited

U.S. PATENT DOCUMENTS

2013/0286047 A1* 10/2013 Katano .............. H04N 5/23218
                                                  348/333.01
2016/0144236 A1*  5/2016 Ko ......................... G16H 20/30
                                                  434/247
2017/0296874 A1* 10/2017 Zamir ................ G09B 19/0092

* cited by examiner

EXERCISE INFORMATION MANAGEMENT SYSTEM AND METHOD OF CONTROLLING THE SAME

CROSS-REFERENCE TO RELATED APPLICATION(S)

This application is based on and claims priority under 35 U.S.C. § 119 to Korean Patent Application No. 10-2020-0045980, filed on Apr. 16, 2020, the disclosure of which is incorporated by reference in its entirety.

TECHNICAL FIELD

The disclosure relates to an exercise information management system, and more particularly, to an exercise information management system for managing user's exercise information based on a smart mirror, and a method of controlling the exercise information management system.

BACKGROUND

A smart mirror may be a device in which IT technology is incorporated into a mirror, and the mirror reflects a user's appearance in a basic form. In addition, the smart mirror also acts as a display for information to the user. The display of the smart mirror may support a touch method to allow the user to input desired information to the smart mirror. In other words, the smart mirror performs a role of the mirror and performs functions as the display and an input device as needed.

The smart mirror may be used as an exercise system based on a body recognition. Since an existing exercise system using the smart mirror is composed of a single terminal of a stand-alone type, a service to the existing user is stopped when the user moves a seat or another user occupies the terminal due to a nature of a movement.

SUMMARY

An aspect of the disclosure is to enable all of a plurality of smart mirrors to share and manage exercise information of a single user. Additional aspects of the disclosure will be set forth in part in the description which follows and, in part, will be obvious from the description, or may be learned by practice of the disclosure.

In accordance with an aspect of the disclosure, an exercise information management system may include a plurality of smart mirrors; and a server configured to communicate with at least one smart mirror. Exercise-related information of an exercise performed by a user in the at least one smart mirror among the plurality of smart mirrors is stored in the server; and the remaining smart mirrors among the plurality of smart mirrors is configured to share the exercise-related information stored in the server.

The exercise-related information may include the user's body measurement information measured by the at least one smart mirror among the plurality of smart mirrors. The body measurement information may include at least one of the user's somatotype measurement information and muscle measurement information. The exercise-related information may further include body history information generated by a comparison of the body measurement information measured by one of the plurality of smart mirrors and the body measurement information measured by another smart mirror.

Additionally, the exercise-related information may include exercise prescription information generated by the server based on the body measurement information. The exercise-related information may further include a progress of the exercise performed by the user in at least one of the plurality of smart mirrors. The server may be configured to store user information for user authentication. The exercise-related information may be shared with a mobile device owned by the user through user authentication in addition to the plurality of smart mirrors. The smart mirror may include a capturing device configured to capture the user reflected in a mirror; a user interface configured to input information required for user authentication; and a display configured to display the information.

In accordance with another aspect of the disclosure, in a method of controlling an exercise information management system, the exercise information management system including a plurality of smart mirrors, and a server configured to communicate with at least one smart mirror. The method may include storing exercise-related information of an exercise performed by a user in the at least one smart mirror among the plurality of smart mirrors in the server; and sharing the exercise-related information stored in the server in the remaining smart mirrors among the plurality of smart mirrors.

The exercise-related information may include the user's body measurement information measured by the at least one smart mirror among the plurality of smart mirrors. The body measurement information may include at least one of the user's somatotype measurement information and muscle measurement information. The exercise-related information may further include body history information generated by a comparison of the body measurement information measured by one of the plurality of smart mirrors and the body measurement information measured by another smart mirror.

The exercise-related information may further include exercise prescription information generated by the server based on the body measurement information. The exercise-related information may further include a progress of the exercise performed by the user in at least one of the plurality of smart mirrors. The server may be configured to store user information for user authentication. The method may further include sharing the exercise-related information with a mobile device owned by the user through user authentication in addition to the plurality of smart mirrors. Additionally, the smart mirror may include a capturing device configured to capture the user reflected in a mirror; a user interface configured to receive input information required for user authentication; and a display configured to display the information.

In accordance with another aspect of the disclosure, an exercise information management system may include a plurality of smart mirrors having a capturing device configured to capture the user reflected in a mirror, a user interface configured to receive input information required for user authentication, and a display configured to display the information; and a server configured to communicate with at least one smart mirror. Exercise-related information of an exercise performed by a user in the at least one smart mirror among the plurality of smart mirrors may be stored in the server; and the remaining smart mirrors among the plurality of smart mirrors may be configured to share the exercise-related information stored in the server.

The exercise-related information may include the user's body measurement information measured by the at least one smart mirror among the plurality of smart mirrors; body history information generated through comparison of the body measurement information measured by one of the plurality of smart mirrors and the body measurement information measured by another smart mirror; exercise prescription information generated by the server based on the body measurement information; and a progress of the exercise performed by the user in at least one of the plurality of smart mirrors. The body measurement information may include at least one of the user's somatotype measurement information and muscle measurement information.

BRIEF DESCRIPTION OF THE DRAWINGS

These and/or other aspects of the disclosure will become apparent and more readily appreciated from the following description of the exemplary embodiments, taken in conjunction with the accompanying drawings of which.

DETAILED DESCRIPTION

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor and is specifically programmed to execute the processes described herein. The memory is configured to store the modules and the processor is specifically configured to execute said modules to perform one or more processes which are described further below.

Furthermore, control logic of the present invention may be embodied as non-transitory computer readable media on a computer readable medium containing executable program instructions executed by a processor, controller/control unit or the like. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Figure 1:
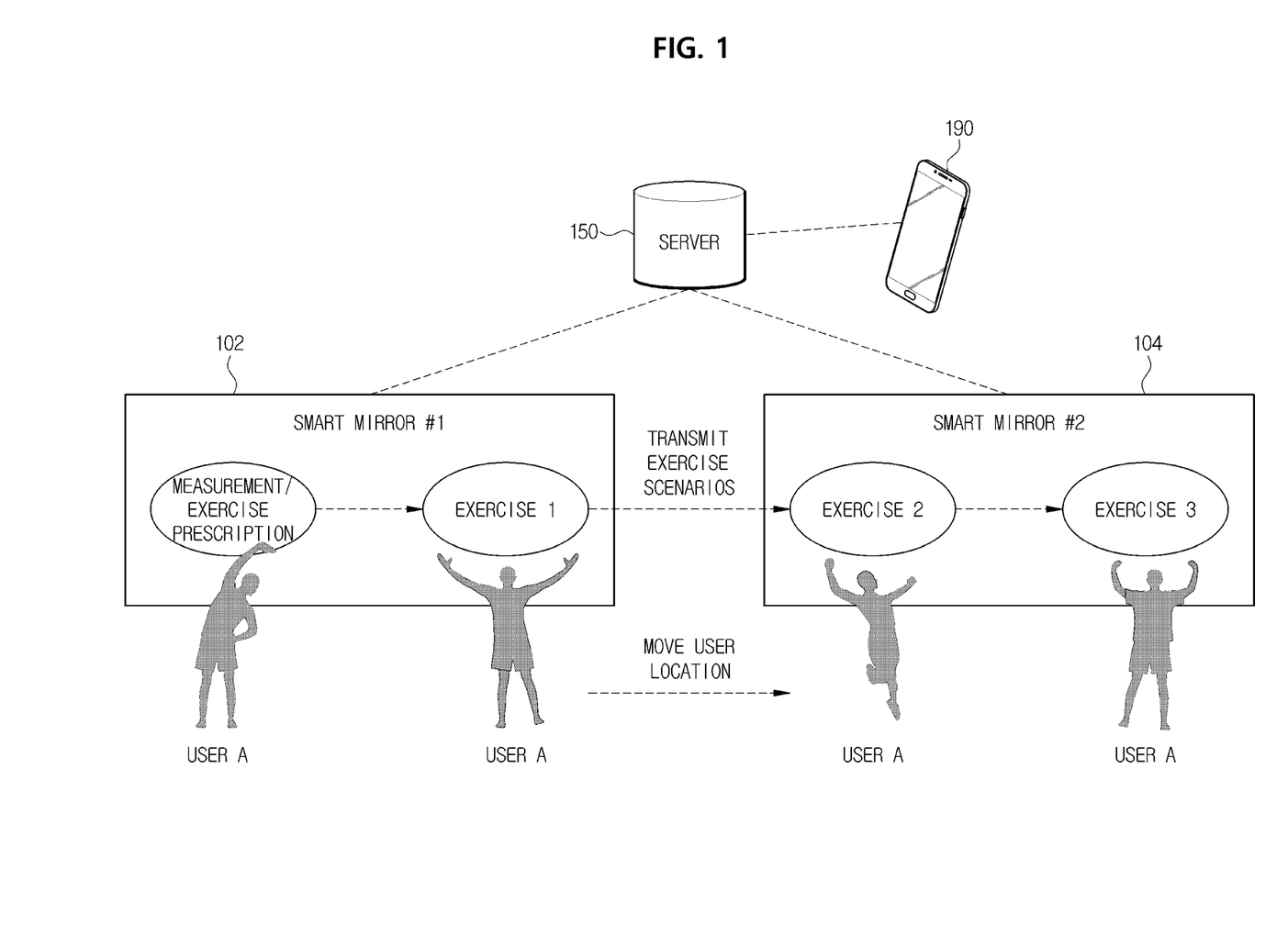
FIG. 1 is a view illustrating an exercise information management system according to an exemplary embodiment.

FIG. 1 is a view illustrating an exercise information management system according to an exemplary embodiment. Referring to FIG. 1, in an exercise information management system, a plurality of smart mirrors 102 and 104 may be connected to be communicatively connected to a server 150, and a mobile device 190 of a user may be connected to the server 150 to enable communication.

The smart mirrors 102 and 104 may be devices in which IT technology is incorporated to a mirror while the mirror is still capable of reflecting the user's appearance. In addition, the smart mirrors 102 and 104 may perform a function of capturing the user's appearance and storing the user's appearance as image data, a function as a display for showing information such as an image or text to the user, and a function as a communication device configured to communicate with a server 150 and the mobile device 190. The smart mirrors 102 and 104 of the exercise information management system may be installed in a fitness center (Gym) or at home, allowing the user to exercise while looking at the smart mirrors 102 and 104, and results of analyzing the user's exercise content may be displayed through the smart mirrors 102 and 104 to allow the user to check the results.

In the exercise information management system, in particular, by sharing or exchanging exercise information between the plurality of smart mirrors 102 and 104, the user may manage exercise results through the plurality of smart mirrors 102 and 104 without limitation of a place and a time. In other words, as illustrated in FIG. 1, the user (single user A) may measure his or her physical condition in the smart mirror 102 and perform the corresponding exercise (exercise 1) after receiving an instruction for an exercise suitable for the measured physical condition. As described above, an exercise performed by the user for the smart mirror 102 may be transmitted from the smart mirror 102 (e.g., a first smart mirror) to another smart mirror 104 (e.g., a second smart mirror). The user (the same user A) may perform another exercise (Exercise 2 and Exercise 3) for the smart mirror 104 located in a different place. The exercises (exercise 2 and exercise 3) conducted on the smart mirror 104 may be shared directly with the smart mirror 102 or transmitted to the server 150 to allow the smart mirrors 102 and 104 and the mobile device 190 to share the exercise information with each other. In particular, the user may continue to perform subsequent exercises (e.g., exercise 2 and exercise 3) associated with a previous exercise for the smart mirror 104 in another place by referring to the results of exercise performed on the smart mirror 102. The exercise in the smart mirror 102 and the exercise in the smart mirror 104 may be completely irrelevant.

As described above, in the exercise information management system, for example, the results of exercising on the smart mirror installed in the fitness center (for example, the smart mirror 102) may be checked and referenced through another smart mirror installed in the home (for example, the smart mirror 104) to perform the exercise on the smart mirror at home.

Figure 2:
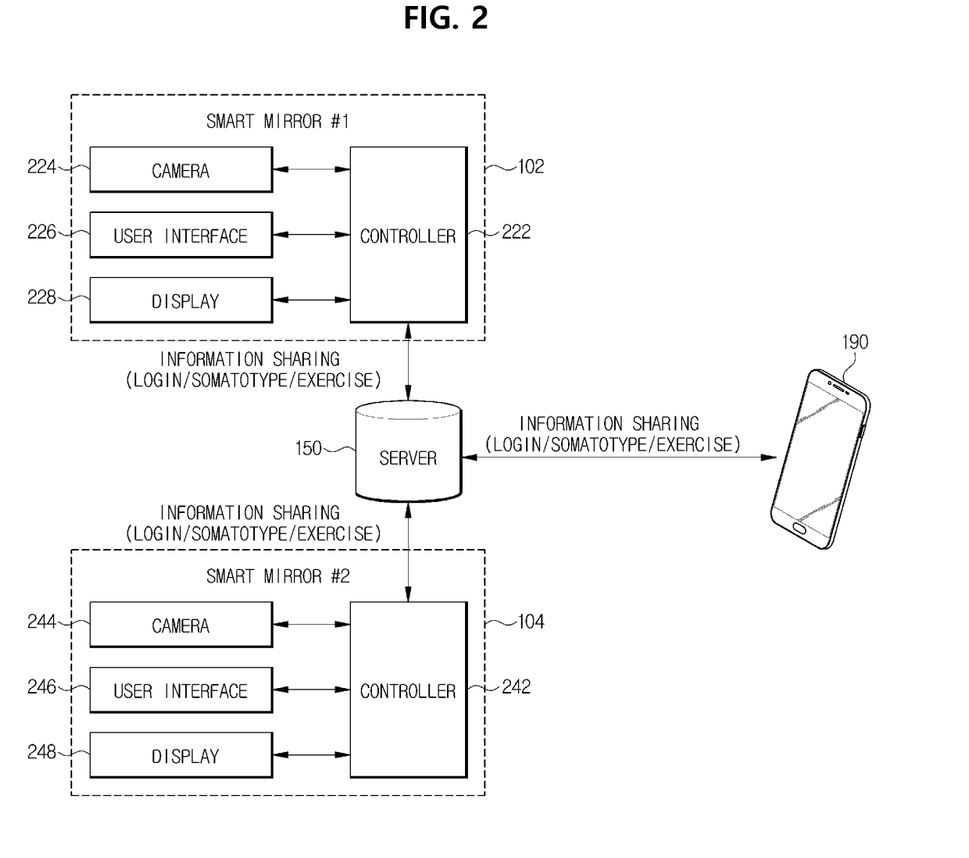
FIG. 2 is a view illustrating a configuration of a smart mirror of an exercise information management system according to an exemplary embodiment.

FIG. 2 is a view illustrating a configuration of a smart mirror of an exercise information management system according to an exemplary embodiment. Since the smart mirrors 102 and 104 illustrated in FIG. 2 are configured identically to each other, a configuration will be described with reference to the smart mirror 102. As illustrated in FIG. 2, the smart mirror 102 may include a controller 222, a camera (e.g., capturing or imaging device) 224, a user interface 226, and a display 228.

The controller 222 may be configured to execute an overall operation of the smart mirror 102. In other words, the controller 222 may be configured to operate the camera 224 and the user interface 226 and the display 228, communicate with the server 150, and analyze an image captured using the camera 224. The camera 224 may be configured to capture the user exercising in front of the smart mirror 102. The user's image captured by the camera 224 may capture the user's physical condition (somatotype) as well as the user's exercise posture. The image captured by the camera 224 may be analyzed by the controller 222 and used to determine the user's health index and exercise status.

The user interface 226 is an input device, and may include a password inputter and a biometric information inputter for user authentication. The smart mirror 102 of the exercise information management system may support a touch input, and thus, a password may be entered on a graphic displayed on the display 228 of the smart mirror 102 or user identification information may be input. In addition, after the user's face is captured using the camera 224, the user authentication may be performed through facial recognition in the user interface 226. Accordingly, the user authentication may be performed through fingerprint recognition.

The display 228 may use a mirror portion of the smart mirror 102 as a display device. For this, the mirror portion of the smart mirror 102 may be implemented as a half mirror. In other words, a transmittance of the mirror portion of the smart mirror 102 may be adjusted for the mirror to function like a mirror normally, but when the image or text is to be displayed, it may function as the display device.

The controller 222 of the smart mirror 102 may be configured to communicate with the server 150 to share various information. For example, information related to login information (user authentication information), the user's somatotype (image), and the exercise (type and result, etc.) may be transmitted to the server 150 to share information with another smart mirror 104. Of course, the smart mirror 102 may also share information of another smart mirror 104 via the server 150. The information of the server 150 may also be shared with the mobile device 190 owned by the user. Another smart mirror 104 of FIG. 2 may also include a controller 242, a camera 244, a user interface 246, a display 248, and the like, like the smart mirror 102 described above, and may operate in the same manner as the smart mirror 102 based on this configuration.

Figure 3:
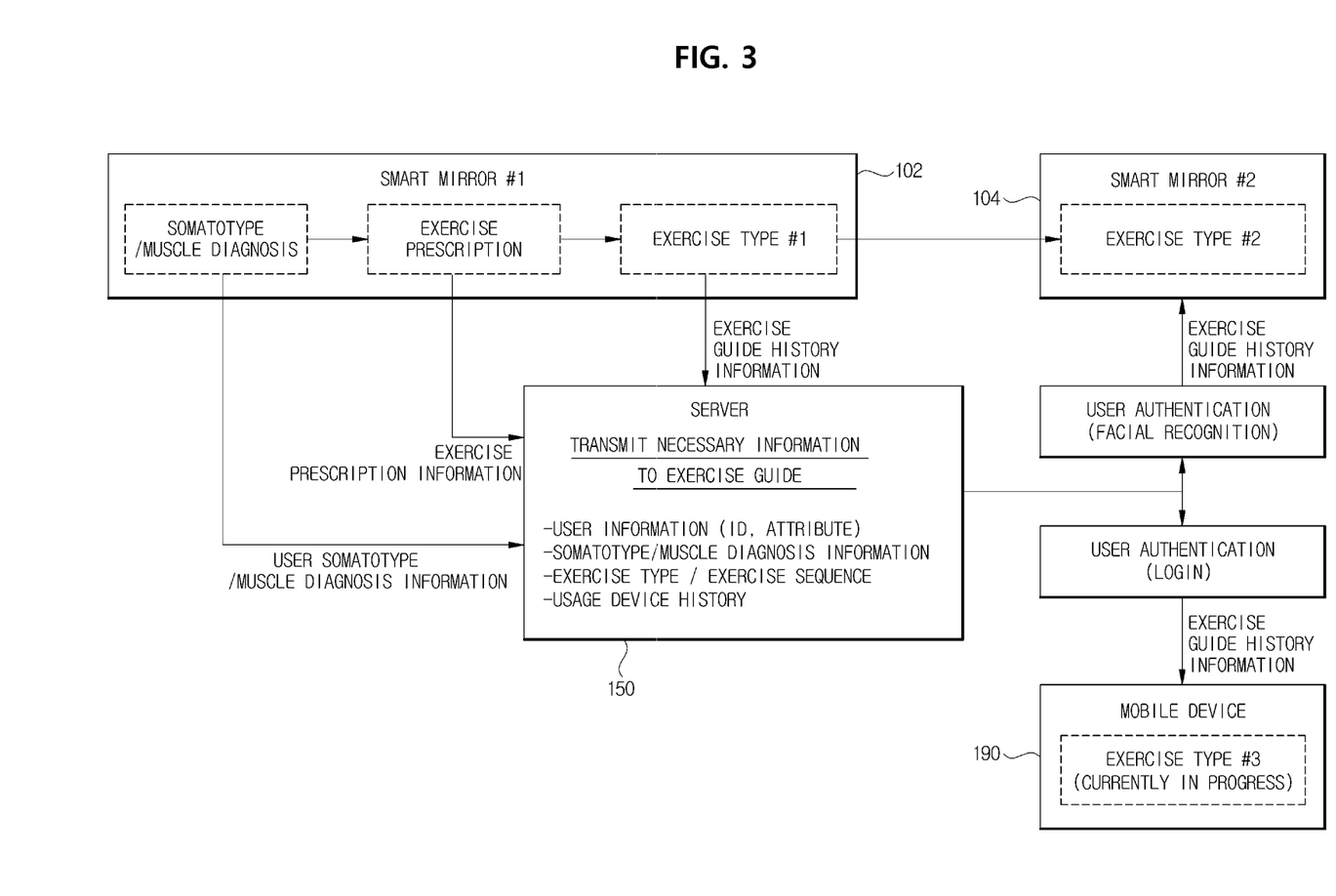
FIG. 3 is a view illustrating a concept of sharing exercise information of an exercise information management system according to an exemplary embodiment.

FIG. 3 is a view illustrating a concept of sharing exercise information of an exercise information management system according to an exemplary embodiment. Referring to FIG. 3, the smart mirror 102 may be configured to diagnose the user's somatotype or muscle mass through analysis of the image captured by the user, and transmit the diagnosis result, that is, diagnosis information of the user's somatotype/muscle to the server 150. In addition, the smart mirror 102 may be configured to prescribe or generate an exercise suitable for the user based on the result of diagnosis of the somatotype/muscle, and transmit exercise prescription information to the server 150. The user may perform the generated exercise routine (for example, exercise type #1) in front of the smart mirror 102, and the smart mirror 102 may guide the user to effectively perform the exercise. Exercise guide history information performed by the smart mirror 102 may be also transmitted to the server 150. Even if the same user moves to another smart mirror, the exercise guide generated in one smart mirror may be displayed and guided subsequently in another smart mirror after user login and authentication. Accordingly, a user may move to another smart mirror and continue an exercise there.

After completing the exercise (exercise type #1) for the smart mirror 102, the user may relocate to another mirror 104 and perform another exercise (for example, exercise type #2). In particular, the user may perform the user authentication on the smart mirror 104 so that the exercise guide history information of the exercise performed by the smart mirror 102 from the server 150 is transmitted to the smart mirror 104. In other words, the user may utilize the information related to the exercise performed by the smart mirror 102 through the user authentication in another smart mirror 104. The user authentication may be, for example, facial recognition.

In addition, the user may exercise through the mobile device 190. Even in this case, the user may perform the user authentication for the mobile device 190 so that the exercise guide history information of the exercise performed by the smart mirror 102 and 104 from the server 150 is transmitted to the mobile device 190. In other words, the user may utilize the information related to the exercise performed by the smart mirrors 102 and 104 through the user authentication on the mobile device 190. The user authentication may be, for example, login through ID and password input.

The smart mirror 102 may also perform the user authentication if necessary. Accordingly, the server 150 may be configured to store user information (ID, characteristic), somatotype/muscle diagnosis information, exercise type/sequence information, and usage device history information, and may be shared by devices such as the smart mirrors 102, 104 and the mobile device 190. The used device history may be the storage and sharing of the contents of the user's use of the smart mirror.

Figure 4A:
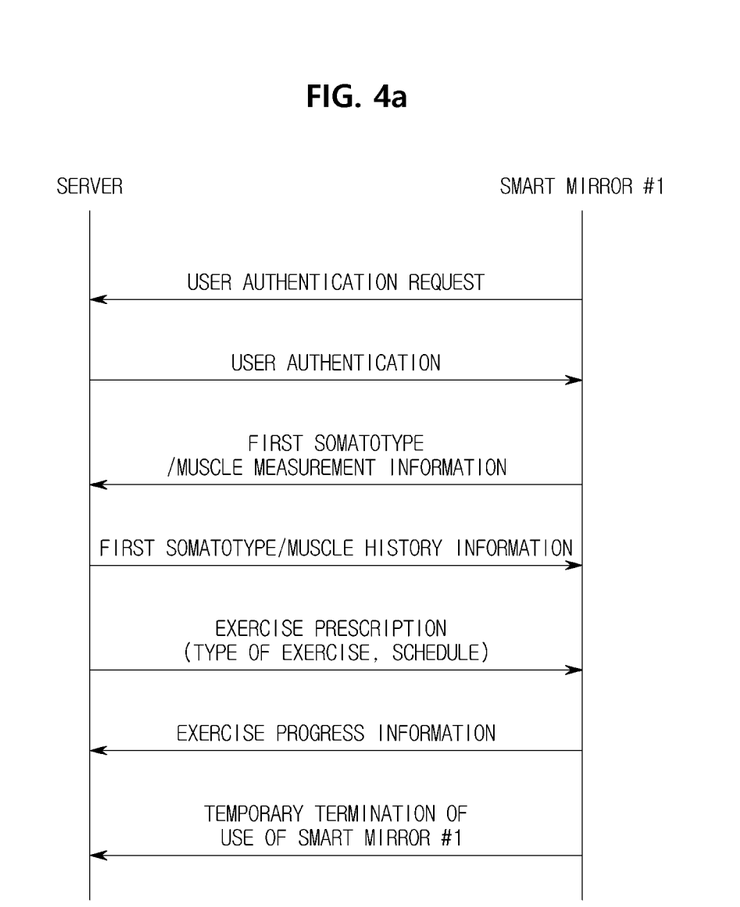
FIGS. 4A-4D are views illustrating control and data flow of an exercise information management system according to an exemplary embodiment.

FIGS. 4A-4D are views illustrating control and data flow of an exercise information management system according to an exemplary embodiment. First, FIG. 4A is a view illustrating control and data flow between the server and a smart mirror #1. When the user requests the user authentication through the smart mirror #1, the server 150 may refer to or access user information data stored in the server 150 and perform the user authentication only for the authenticated user.

When first somatotype/muscle measurement information, which is information measuring the user's somatotype/muscle in the smart mirror #1, may be transmitted to the server 150, the server 150 may be configured to compare the first somatotype/muscle measurement information transmitted from the smart mirror #1 with previous somatotype/muscle measurement information of the same user, and transmit first somatotype/muscle history information analyzed for the difference is transmitted to the smart mirror #1. In particular, the previous somatotype/muscle measurement information may be the same user's body shape/muscle measurement information measured by another smart mirror.

The server 150 may be configured to generate the exercise type or routine and schedule based on the user's first somatotype/muscle measurement information measured by the smart mirror #1 and transmit the generated exercise type or routine and schedule to the smart mirror #1. The user may exercise according to the exercise generation of the server 150, and an exercise progress of the user may be captured by the camera in the smart mirror #1 or secured through the user's input and transmitted to the server 150. When the user's exercise terminates, the user temporarily terminates the use of the smart mirror #1 through the user interface, and the contents may be transmitted to the server 150.

Figure 4B:
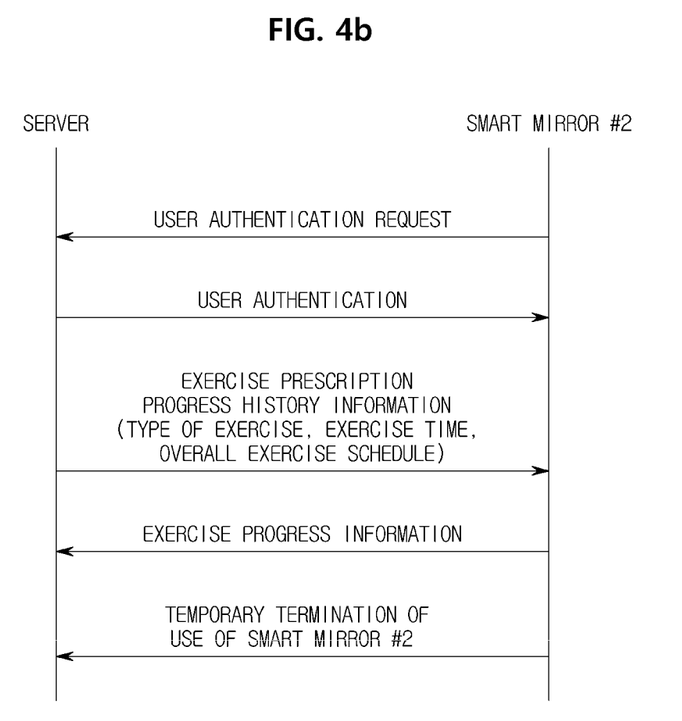

FIG. 4B is a view illustrating control and data flow between the server and a smart mirror #2. When the user moves to the location and the user authentication is requested through the smart mirror #2 installed elsewhere for exercise, the server 150 may refer to the user information data stored in the server 150 and perform the user authentication only for the authenticated user.

The server 150 may be configured to transmit exercise generated progress history information in the smart mirror #1 to the smart mirror #2. The exercise generated progress history information in the smart mirror #1 may include the generated exercise, exercise schedule, and exercise progress history of the server 150 when the user uses the smart mirror #1. The user may subsequently perform a follow-up exercise linked to the exercise performed in the smart mirror #1 in the smart mirror #2 based on the exercise generated progress history information transmitted from the server 150 to the smart mirror #2. The progress of the user's exercise in the smart mirror #2 may be captured by the camera in the smart mirror #2 or secured through the user input and transmitted to the server 150. When the user's exercise terminates, the user temporarily terminates the use of the smart mirror #2 through the user interface, and the contents may be transmitted to the server 150.

Figure 4C:
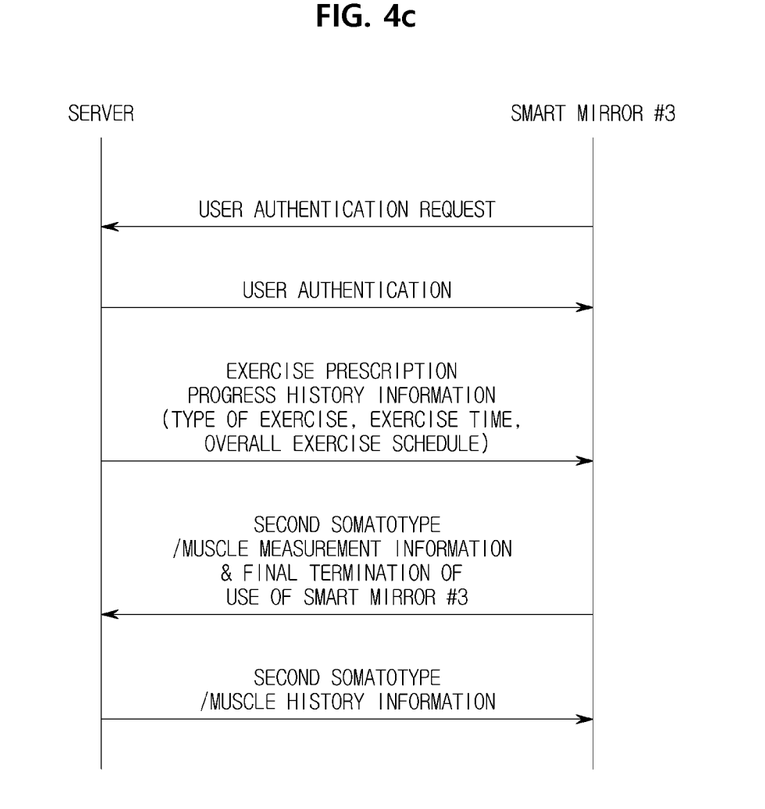

FIG. 4C is a view illustrating control and data flow between the server and a smart mirror #3. When the user moves to another location and requests the user authentication through the smart mirror #3 installed in another location for exercise, the server 150 may refer to the user information data stored in the server 150 and perform the user authentication only for the authenticated user.

The server 150 may be configured to transmit the exercise generated progress history information in the smart mirror #2 to the smart mirror #3. The exercise generated progress history information in the smart mirror #2 may include the generated exercise, exercise schedule, and exercise progress history of the server 150 when the user uses the smart mirror #2. The user may subsequently perform the follow-up exercise linked to the exercise performed in the smart mirror #2 in the smart mirror #3 based on the exercise generated progress history information transmitted from the server 150 to the smart mirror #3. The progress of the user's exercise in the smart mirror #3 may be captured by the camera in the smart mirror #3 or secured through the user input and transmitted to the server 150.

When the measurement of the user's somatotype/muscle is performed in the smart mirror #3, the smart mirror #3 may be configured to transmit the measured second somatotype/muscle measurement information to the server 150. The server 150 may be configured to compare the second somatotype/muscle measurement information transmitted from the smart mirror #3 with the previous somatotype/muscle measurement information of the same user, and transmit the second somatotype/muscle measurement information analyzing the difference to the smart mirror #3. In particular, the previous somatotype/muscle measurement information may be the somatotype/muscle measurement information of the same user measured by another smart mirror.

When the user's exercise terminates, the user finally terminates the use of the smart mirror #3 through the user interface, and the contents may be transmitted to the server 150. When the authentication request from the same user does not occur in another smart mirror within a preset time after the use of smart mirror #3 is temporarily terminated, it may be processed as a final termination in smart mirror #3.

Figure 4D:
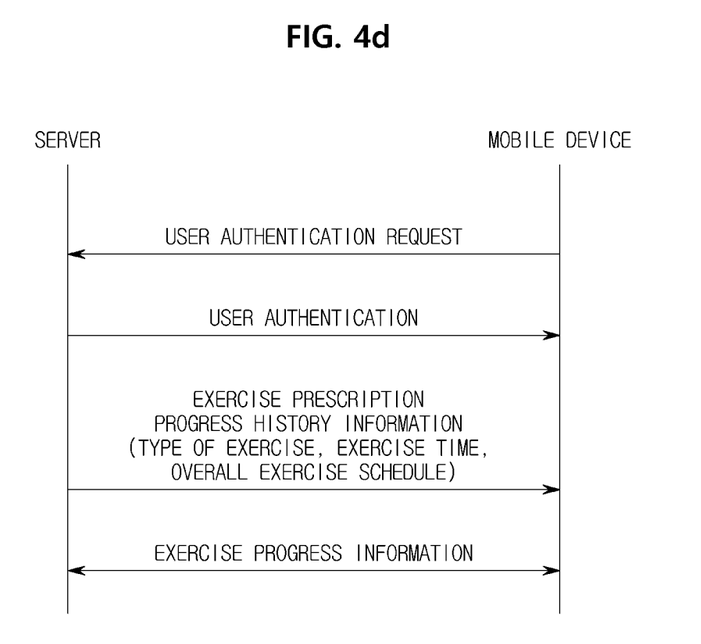

FIG. 4D is a view illustrating control and data flow between the server and the mobile device. When the user requests the user authentication through the mobile device, the server 150 may refer to user information data stored in the server 150 and perform the user authentication only for the authenticated user.

The server 150 may be configured to transmit the exercise generated progress history information from the most recently used smart mirror #3 to the mobile device. The exercise generated progress history information in the smart mirror #3 may include the generated exercise, exercise schedule, and exercise progress history of the server 150 when the user uses the smart mirror #3. The user may subsequently perform the follow-up exercise linked to the exercise performed in smart mirror #3 in the mobile device based on the exercise generated progress history information transmitted from the server 150 to the mobile device. The progress of the user's exercise in the mobile device may be captured by the camera in the mobile device or secured through the user input and transmitted to the server 150.

As illustrated in FIGS. 4A-4D, the exercise information management system according to the exemplary embodiment of the disclosure may allow at least one smart mirror and the mobile device to share and manage the exercise information of the single user.

According to the exemplary embodiments of the disclosure, the exercise information of the single user occurring in the plurality of smart mirrors may be shared and managed by all of the plurality of smart mirrors.

The disclosed exemplary embodiments is merely illustrative of the technical idea, and those skilled in the art will appreciate that various modifications, changes, and substitutions may be made without departing from the essential characteristics thereof. Therefore, the exemplary embodiments disclosed above and the accompanying drawings are not intended to limit the technical idea, but to describe the technical spirit, and the scope of the technical idea is not limited by the embodiments and the accompanying drawings. The scope of protection shall be interpreted by the following claims, and all technical ideas within the scope of equivalent shall be interpreted as being included in the scope of rights.

What is claimed is:

1. An exercise information management system, comprising:
    a plurality of smart mirrors comprising at least a first smart mirror and a second smart mirror; and
    a server configured to communicate with the plurality of smart mirrors, store exercise-related information of an exercise performed by a user of the first smart mirror, and share the exercise-related information with the second smart mirror,
    wherein the exercise-related information is configured to be shared directly between the first smart mirror and the second smart mirror or transmitted to the server to allow sharing between the first smart mirror and the second smart mirror, and
    wherein the first smart mirror and the second smart mirror each include a display configured to display the exercise-related information that is shared between the first and second smart mirrors.

2. The exercise information management system according to claim 1, wherein the exercise-related information includes body measurement information of the user measured by the at least one smart mirror among the plurality of smart mirrors.

3. The exercise information management system according to claim 2, wherein the body measurement information include at least one of a somatotype measurement information and muscle measurement information of the user.

4. The exercise information management system according to claim 1, wherein the exercise-related information further includes exercise information generated by the server based on the body measurement information.

5. The exercise information management system according to claim 1, wherein the exercise-related information further includes a progress of the exercise performed by the user in at least one of the plurality of smart mirrors.

6. The exercise information management system according to claim 1, wherein the server is configured to store user information for user authentication.

7. The exercise information management system according to claim 1, wherein the exercise-related information is shared with a mobile device of the user through user authentication in addition to the plurality of smart mirrors.

8. The exercise information management system according to claim 1, wherein each smart mirror includes:
    a capturing device configured to capture the user reflected in a mirror; and
    a user interface configured to input information required for user authentication.

9. The exercise information management system according to claim 1, wherein the exercise-related information includes body history information generated through comparison of first body measurement information measured by the first smart mirror and second body measurement information measured by the second smart mirror.

10. A method of controlling an exercise information management system, the exercise information management system including a plurality of smart mirrors comprising at least a first smart mirror and a second smart mirror, and a server configured to communicate with the first smart mirror and the second smart mirror, the method comprising:
    storing, by a processor, exercise-related information of an exercise performed by a user of the first smart mirror in the server; and
    sharing, by the processor, the exercise-related information stored in the server with the second smart mirror,
    wherein the exercise-related information is configured to be shared directly between the first smart mirror and the second smart mirror or transmitted to the server to allow sharing between the first smart mirror and the second smart mirror, and
    wherein the first smart mirror and the second smart mirror each include a display configured to display the exercise-related information that is shared between the first and second smart mirrors.

11. The method according to claim 10, wherein the exercise-related information includes body measurement information of the user measured by the at least one smart mirror among the plurality of smart mirrors.

12. The method according to claim 11, wherein the body measurement information includes at least one of somatotype measurement information and muscle measurement information of the user.

13. The method according to claim 10, wherein the exercise-related information further includes exercise information generated by the server based on the body measurement information.

14. The method according to claim 10, wherein the exercise-related information further includes a progress of the exercise performed by the user in at least one of the plurality of smart mirrors.

15. The method according to claim 10, wherein the server is configured to store user information for user authentication.

16. The method according to claim 10, further comprising:
    sharing, by the processor, the exercise-related information with a mobile device owned by the user through user authentication in addition to the plurality of smart mirrors.

17. The method according to claim 10, wherein each smart mirror includes:
    a capturing device configured to capture the user reflected in a mirror; and
    a user interface configured to input information required for user authentication.

18. The method according to claim 10, wherein the exercise-related information includes body history information generated through comparison of first body measurement information measured by the first smart mirror and second body measurement information measured by the second smart mirror.

19. An exercise information management system, comprising:
    a plurality of smart mirrors comprising at least a first smart mirror and a second smart mirror each including a capturing device configured to capture a user reflected in a mirror, a user interface configured to input information required for user authentication; and
    a server configured to store exercise-related information of an exercise performed by the user of the first smart mirror, and share the exercise-related information with the second smart mirror, wherein the exercise-related information is configured to be shared directly between the first smart mirror and the second smart mirror or transmitted to the server to allow sharing between the first smart mirror and the second smart mirror,
    wherein the exercise-related information includes:
        body measurement information of the user measured by the at least one smart mirror among the plurality of smart mirrors;
        body history information generated through a comparison of the body measurement information measured by one of the plurality of smart mirrors and the body measurement information measured by another smart mirror;
        exercise information generated by the server based on the body measurement information; and
        a progress of the exercise performed by the user in at least one of the plurality of smart mirrors; and
    wherein the first smart mirror and the second smart mirror each include a display configured to display the exercise-related information that is shared between the first and second smart mirrors.

20. The exercise information management system according to claim 19, wherein the body measurement information includes at least one of somatotype measurement information and muscle measurement information of the user.

* * * * *